United States Patent
Li et al.

(10) Patent No.: US 9,850,194 B2
(45) Date of Patent: Dec. 26, 2017

(54) PROCESS FOR DOUBLE CARBONYLATION OF ALLYL ALCOHOLS TO CORRESPONDING DIESTERS

(71) Applicant: EVONIK DEGUSSA GMBH, Essen (DE)

(72) Inventors: Haoquan Li, Zhongshan (CN); Jie Liu, Zhuzhou (CN); Matthias Beller, Ostseebad Nienhagen (DE); Ralf Jackstell, Cuxhaven Altenwalde (DE); Robert Franke, Marl (DE); Katrin Marie Dyballa, Recklinghausen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/378,514

(22) Filed: Dec. 14, 2016

(65) Prior Publication Data

US 2017/0174610 A1   Jun. 22, 2017

(30) Foreign Application Priority Data

Dec. 16, 2015 (EP) .................................... 15200490

(51) Int. Cl.
*C07C 67/00* (2006.01)
*C07C 67/38* (2006.01)

(52) U.S. Cl.
CPC .................... *C07C 67/38* (2013.01)

(58) Field of Classification Search
CPC .................................................... C07C 67/38
See application file for complete search history.

(56) References Cited

U.S. PATENT DOCUMENTS

| 4,238,419 A | 12/1980 | Matsumoto et al. |
| 4,567,305 A | 1/1986 | Matsumoto et al. |
| 6,127,584 A | 10/2000 | Zajacek et al. |
| 6,225,509 B1 | 5/2001 | Dubner et al. |
| 7,271,295 B1 | 9/2007 | White et al. |

FOREIGN PATENT DOCUMENTS

| CA | 1242741 | 10/1988 |
| EP | 0146859 | 7/1985 |
| WO | 2012/163831 | 12/2012 |

OTHER PUBLICATIONS

Tsuji et al. Organic Syntheses by Means of Noble Metal Compounds. VIII. Catalytic Carbonylation of Allylic Compounds with Palladium Chloride. J. Am. Chem. Soc. 1964, 86, 4350-4353.
Pittman et al. Rhodium-Catalyzed Hydroformylation of Allyl Alcohol. A Potential Route to 1,4-Butanediol. J. Org. Chem. 1980, 45, 2132-2139.
Satoh, et al. Palladium-Catalyzed Carbonylation of Allyl Alcohols in the Presence of Phenols. J. Org. Chem. 1997, 62, 2662-2664.
International Search Report for EP 15 20 0490 dated May 19, 2016 (1 page).
Knifton, John F. Syngas Reactions: II The homogeneous catalyzed carbonylation and cyclization of all allylic substrates. Journal of Organometallic Chemistry. 188, 1980, pp. 223-236.
Liu, Qiang, et al. Domino Catalysis: Palladium-Catalyzed Carbonylation of Allylic Alcohols to β, γ-Unsaturated Esters. Angewandte Chemie International Edition, 2013, 52, pp. 8064-8068.
Itoh, Kenji, et al. Palladium-catalyzed carbonylation of allyl alcohols in the presence of lithium chloride and titanium(IV) isopropoxide. Journal of Molecular Catalysis. 75, 1992, pp. 117-122.

*Primary Examiner* — Yevegeny Valenrod
*Assistant Examiner* — Blaine G Doletski
(74) *Attorney, Agent, or Firm* — Smith, Gambrell & Russell, LLP

(57) ABSTRACT

The invention relates to a process for doubly carbonylating allyl alcohols to the corresponding diesters, wherein a linear or branched allyl alcohol is reacted with a linear or branched alkanol (alcohol) with supply of CO and in the presence of a catalytic system composed of a palladium complex and at least one organic phosphorus ligand and in the presence of a hydrogen halide selected from HCl, HBr and HI.

11 Claims, No Drawings

PROCESS FOR DOUBLE CARBONYLATION OF ALLYL ALCOHOLS TO CORRESPONDING DIESTERS

The invention relates to a process for doubly carbonylating allyl alcohols to the corresponding diesters, wherein a linear or branched allyl alcohol is reacted with a linear or branched alkanol (alcohol) with supply of CO and in the presence of a catalytic system composed of a palladium complex and at least one organic phosphorus ligand and in the presence of a hydrogen halide selected from HCl, HBr and HI.

There exist a multitude of methods that are of significance for the synthesis of specific esters. Allyl alcohol in particular is a sustainable organic compound which has already found wide use. For example, the direct carbonylation of the CO unit in order to synthesize β,γ-unsaturated carboxylic acid derivatives was studied for the first time in 1964 by Tsuji [J. Tsuji, J. Kiji, S. Imamura, M. Morikawa, *J. Am. Chem. Soc.* 1964, 86, 4350-4353]. Here, various allyl compounds such as allyl chloride, allyl bromide, allyl ethers and allyl alcohol were converted successively to the corresponding β,γ-unsaturated carboxylic esters in the presence of palladium chloride under CO pressure. Allyl alcohol is used in industry particularly also for preparation of butane-1,4-diol by hydrogenation of the hydroformylation product thereof [a) J. C. Pittman, W. Honnick, *J. Org. Chem.* 1980, 45, 2132-2139; b) D. ARLT, (UMICORE AG & CO. KG), WO 2012/163831, 2012; c) W. S. Dubner, W. P.-s. Shum (ARCO Chemical Technology, L.P.), U.S. Pat. No. 6,225,509 B1, 2001; d) M. Matsumoto, M. Tamura, (Kuraray Co., Ltd.), U.S. Pat. No. 4,238,419 A, 1980; e) M. Matsumoto, S. Miura, K. Kikuchi, M. Tamura, H. Kojima, K. Koga, S. Yamashita, (Kuraray Company, Ltd. Daicel Chemical Industries, Ltd.), U.S. Pat. No. 4,567,305 A, 1986; f) D. F. White, W. S. Dubner, (Lyondell Chemical Technology, L.P. (Greenville, Del., US)), U.S. Pat. No. 7,271,295 B1, 2007; g) J. G. Zajacek, W. P. Shum, (Arco Chemical Technology, L.P.), U.S. Pat. No. 6,127,584 B1, 2000].

In 1980, a catalyst system in combination of palladium halide such as $PdCl_2$, $PdBr_2$, a phosphine ligand, for example $PPh_3$, $P(p-Tol)_3$ and cocatalysts such as $CaCl_2$ and $CoCl_2$ was published for the carbonylation of allylic compounds, for example allyl chloride, allyl bromide and allyl alcohols [J. F. Knifton, *J. Organomet. Chem.* 1980, 188, 223-236]. In 1992, a similar study by Miura and co-workers in the presence of lithium chloride and titanium isopropoxide as reaction promoter was described as a further example of the carbonylation of allyl alcohol [K. Itoh, N. Hamaguchi, M. Miura, M. Nomura, *J. Mol. Catal.* 1992, 75, 117-122]. In 1997, the reaction in the presence of phenol was reported [T. Satoh, M. Ikeda, Y. Kushino, M. Miura, M. Nomura, *J. Org. Chem.* 1997, 62, 2662-2664]. In 2013, a more general and practical method for the alkoxycarbonylation of allyl alcohol was described by Beller et al. (Equation 1) [Q. Liu, L. Wu, H. Jiao, X. Fang, R. Jackstell, M. Belier, *Angew. Chem. Int. Ed.* 2013, 52, 8064-8068]. The catalyst system consists of $Pd(OAc)_2$, phosphine ligands, for example Xantphos or $BuPAd_2$, and trifluoroacetic acid. A broad spectrum of substrate spectra was presented, and mechanistic studies were conducted. In all cases reported, the unsaturated C=C bond was conserved after the reaction.

Scheme 1: Alkoxycarbonylation of allyl alcohols

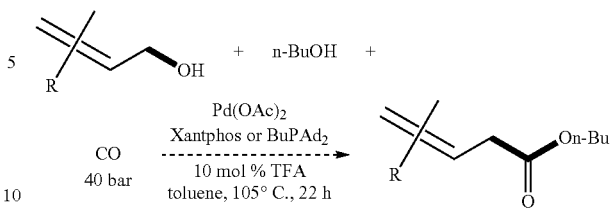

In summary, it can be stated that the selective alkoxycarbonylation of the olefinic unit of allyl alcohols remains a challenge and that there are no known processes for carbonylation of allyl alcohols that lead to diesters. As is well known, diesters are important monomers in the polymer industry for synthesis of polyesters and polyamides via condensation reactions, for example poly(ethylene) adipate and nylon-6,6. The diesters of monomeric compounds can also be used as precursors in the production of dyes, medicaments and agricultural products.

There is therefore a great demand for carboxylic diesters. It is therefore an object of the Invention to find an effective and inexpensive method for synthesis of diesters.

The object is achieved by a process according to Claim 1. The dependent claims constitute preferred process variants. A novel method for synthesis of diesters via a double carbonylation of allyl alcohols is described. The products prepared in accordance with the invention—the diesters—are preferably in the form of isomer mixtures.

The process for doubly carbonylating allyl alcohols to diesters is characterized in that a linear or branched allyl alcohol is reacted with a linear or branched alkanol with supply of CO and in the presence of a catalytic system composed of a palladium complex and at least one organic phosphorus ligand and in the presence of a hydrogen halide selected from HCl, HBr and HI. Preferred hydrogen halides are HCl and HBr. Very particular preference is given to the use of HCl.

Allyl alcohols are preferably compounds of the general formula (1)

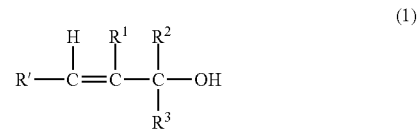

where
$R^1$, $R^2$ and $R^3$ are independently hydrogen or a $C_1$ to $C_{10}$ alkyl radical and R' is hydrogen, or a saturated or unsaturated, branched or unbranched, aliphatic, cycloaliphatic or cycloaliphatic-aliphatic hydrocarbyl radical having up to 12 carbon atoms, in which C—C bonds may be interrupted by oxygen or the —O—CO— group, or a phenyl radical, where the phenyl radical may be substituted as follows: $C_1$- to $C_{10}$-alkyl- or $C_1$- to $C_{10}$-alkoxy groups.

Alkyl is preferably a branched or unbranched radical having 1 to 6 carbon atoms. Alkyl groups are, for example, methyl, ethyl, propyl, isopropyl, 1-butyl, 2-butyl, 1-pentyl, 1-hexyl.

The alcohols used in accordance with the invention may be either primary or secondary alcohols. It is possible to utilize aliphatic, cycloaliphatic, aromatic or else araliphatic alcohols, preference being given to employing aliphatic and araliphatic alcohols. In general, alcohols ROH used in the process according to the invention are those in which the R radical is a $C_1$- to $C_{10}$-alkyl, a $C_1$- to $C_{20}$-cycloalkyl or a $C_7$- to $C_{11}$-aralkyl group.

Phenyl for R' and R in ROH may optionally be substituted by substituents such as $C_1$- to $C_{10}$-alkyl or $C_1$- to $C_{10}$-alkoxy groups.

Preference is given to using alcohols ROH with unsubstituted R radicals. It is of course also possible to use alcohols having a relatively high number of carbon atoms. In particular, lower alkanols ($C_1$ to $C_6$) are used with preference.

Examples of aliphatic alcohols are, for example, methanol, ethanol, 1-propanol, 2-propanol, $C_4$ alcohols, e.g. 1-butanol, 2-butanol or isobutyl alcohol, $C_5$ alcohols, e.g. 1-pentanol, isoamyl alcohol or 2-pentanol, $C_5$ alcohols, e.g. 1-hexanol, 2-methyl-1-pentanol, 3-methyl-1-pentanol, 2,2-dimethyl-1-butanol, 2-ethyl-1-butanol, 4-ethyl-1-pentanol, 2-hexanol, 3-hexanol, 3-methyl-2-pentanol, 2,3-dimethyl-2-butanol, 2-methyl-3-pentanol, 3-methyl-3-pentanol, 4-methyl-2-pentanol, 2-methyl-2-pentanol, $C_7$ alcohols, e.g. n-heptyl alcohol, 2-methyl-1-hexyl alcohol, 3-methyl-1-hexyl alcohol, 4-methyl-1-hexyl alcohol, 5-methyl-1-hexyl alcohol, 2-ethyl-1-pentanol, 3-ethyl-1-pentanol, 2,2-dimethyl-1-pentanol, 3,3-dimethyl-1-pentanol, 4,4-dimethyl-1-pentanol, 2,3-dimethyl-1-pentanol, 2,4-dimethyl-1-pentanol, 3,4-dimethyl-1-pentanol, $C_8$ alcohols, e.g. 1-octanol, 2-methyl-1-heptanol, 3-methyl-1-heptanol, 4-methyl-1-heptanol, 5-methyl-1-heptanol, 2-octanol, 3-octanol, 4-octanol, 2-methyl-2-heptanol, 3-methyl-2-heptanol, 4-methyl-2-heptanol, 5-methyl-2-heptanol, 6-methyl-2-heptanol, 2-methyl-3-heptanol or 3-methyl-3-heptanol, and $C_9$ alcohols, e.g. 1-nonanol.

Examples of the alicyclic alcohols having 4 or more carbon atoms include alicyclic alcohols having 4 to 12 carbon atoms, for example cyclopentanol, cyclohexanol or cyclooctanol.

The $C_7$- to $C_{11}$-aralkyl group used is preferably the benzyl group.

In one variant of the process, the reaction is conducted in the liquid phase at a temperature of 70 to 250° C., preferably at 80 to 180° C., more preferably at temperatures of 80 to 150° C.

The reaction preferably takes place under a pressure of 2 to 100 bar. Preference is given to conducting the reaction under a pressure of 5 to 50 bar.

In one variant of the process, the palladium complex is formed in situ proceeding from a pre-complex, using, as palladium source, palladium-containing salts and complexes as precursor. The palladium compounds may be in different oxidation states, advantageously including the states of 0 to +IV. Preferably, the palladium catalyst is selected from the group comprising Pd acetate, Pd acetylacetonate, Pd halides, Pd-halogen-1,5-cyclooctadienes, Pd nitrates, Pd oxide and diammonium hexachloropalladate.

A particularly preferred precursor is Pd acetylacetonate.

The preferred phosphine ligands L have a mono- or bidentate structure. For example, the ligands L1 to L12 are used particularly advantageously in the process according to the invention:

L1—(9,9-dimethyl-9H-xanthene-4,5-diyl)bis(diphenylphosphine) (=Xantphos),
L2—10,10'-(oxybis(2,1-phenylene))bis(10H-phenoxaphosphinine),
L3—2,2'-((9,9-dimethyl-9H-xanthene-4,5-diyl)bis(tert-butylphosphinediyl))dipyridine,
L4—(oxybis(2,1-phenylene))bis(tert-butyl(phenyl)phosphine),
L5—4,6-bis(diphenylphosphinyl)-10H-phenoxazine,
L6—1,3-bis((diphenylphosphinyl)methyl)benzene,
L7—(oxybis(2,1-phenylene))bis(di-tert-butylphosphine),
L8—(oxybis(2,1-phenylene))bis(di-o-tolylphosphine),
L9—bis(2-(diphenylphosphinyl)-5-methylphenyl)methane,
L10—1,2-bis((di-tert-butylphosphinyl)methyl)benzene,
L11—di(1-adamantyl)-n-butylphosphine,
L12—1-(2-(diphenylphosphinyl)benzyl)-1H-pyrrole.

Xantphos is particularly preferred, especially in combination with Pd acetylacetonate.

The palladium catalyst comprises the phosphine ligand in a ratio of palladium to ligand in the range from 1:1 to 1:20, preferably in the range from 1:1 to 1:10, more preferably in the range from 1:1 to 1:2. The ratio of palladium to hydrogen halide is in the range from 1:3 to 1:30. All ratios are molar ratios.

Effective amounts of catalyst in the process are preferably 0.01 to 12 mol % of palladium based on the allyl alcohol, preference being given to using 0.05 mol % to 1.5 mol % of palladium, based on the allyl alcohol substrate.

It is possible to use solvents for the process according to the invention. For example, polar inert organic solvents or/and water are used. For example, dipolar aprotic solvents, ethers, aliphatic ethers, amides, aromatic compounds, alcohols and esters, and mixtures thereof, are used. Particular preference is given to using aromatic compounds and aliphatic ethers such as toluene and diethyl ether.

Particular preference is given to using, in the process according to the invention, hydrogen chloride as hydrogen halide, preferably in an apolar organic solvent or solvent mixture. More particularly, the reaction is conducted in a mixture of HCl/diethyl ether and a further solvent, preferably toluene.

In a further embodiment of the process, a metal halide, preferably a sodium or lithium halide, e.g. LiBr or LiI, may be added to the reaction. The ratio of metal halide to the hydrogen halide here is preferably 1:1 to 5:1. More preferably, the ratio of halide to hydrogen halide is 1:1 to 2:1. In a particularly advantageous variant, hydrogen chloride is used together with LiBr or LiI.

Surprisingly, it is possible by the process according to the invention to prepare the corresponding diesters, generally in the form of isomer mixtures, but also in the form of preferably n compounds in good yields. Especially via the addition of lithium halides, it is possible to affect the n/iso product ratio in a surprisingly positive manner for formation of n isomers. The process is thus a diester synthesis of high atom and process economy. Four chemical bonds are formed all at once. Surprisingly, yields up to 75% are attained.

The invention is elucidated in detail in examples which follow.

WORKING EXAMPLES

General Remarks:

All commercial reagents were ordered from Alfa Aesar, Aldrich, TCI or Strem. Unless stated otherwise, commercial reagents were used without purification. Allyl alcohol is distilled under reduced pressure prior to use. Toluene, DMF, THF, acetonitrile and methanol are used from the PS-MD-7 solvent purification system from "Innovative technology" using standard Schlenk techniques. Analytical data for the compounds known from the literature were in accordance with data reported. NMR spectra were recorded on the Bruker Avance 300 (300 MHz) NMR spectrometer. Multiplets were assigned as s (singlet), d (doublet), t (triplet), dd (doublet of doublets), m (multiplet) and br s (broad singlet). All measurements were conducted at room temperature, unless stated otherwise. Electron impact (EI) mass spectra were recorded on the AMD 402 mass spectrometer (70 eV). High-resolution mass spectra (HRMS) were recorded on the Agilent 6210 time-of-flight LC/MS (Agilent) with electrospray ionization (ESI). The data are reported as mass units per charge (m/z) and intensities of signals in brackets. The products were separated from the reaction mixture by column chromatography on silica gel 60, 0.063-0.2 mm, 70-230 mesh (Merck).

GC Analysis:

GC analysis was conducted by means of an Agilent GC 7890A gas chromatograph from Agilent Company with a 30 m HP-5 column ((polydimethylsiloxane with 5% phenyl groups, 30 m, 0.32 mm ID, 0.25 μm film thickness). Temperature program: 35° C., 10 min; 10° C./min to 285° C., 5 min; injection volume 1 μl with a split of 50:1.

List of Abbreviations:

BnOH: benzyl alcohol
CyOH: cyclohexanol
equiv.: equivalents
HCl: hydrogen chloride
THF: tetrahydrofuran
T: temperature
p: pressure
Xantphos: 4,5-bis(diphenylphosphinyl)-9,9-dimethylxanthene Example 1

Use of Various Allyl Alcohols (Table 1):

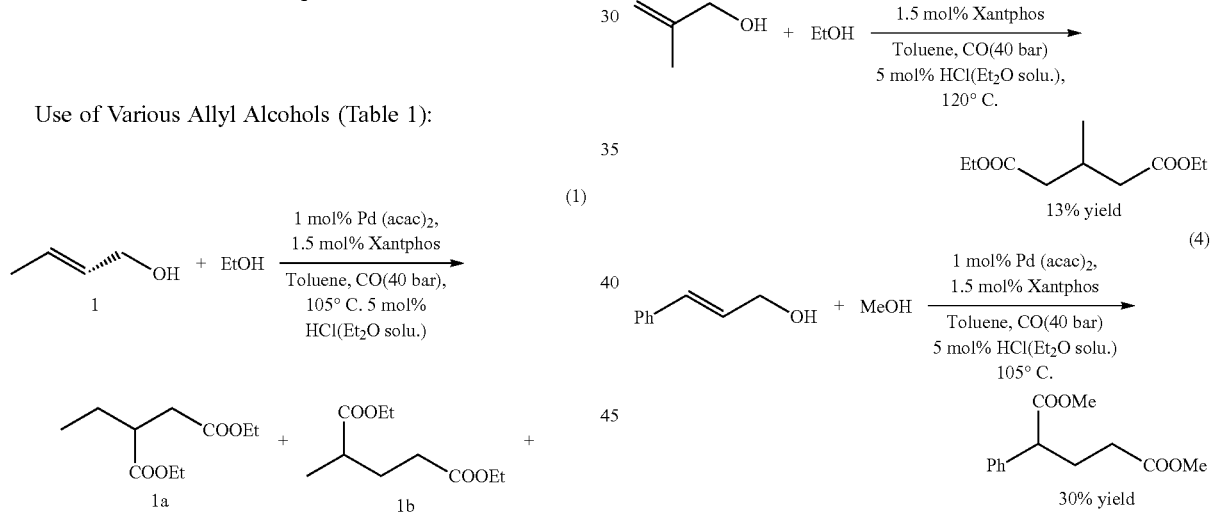

TABLE 1

| Entry | Pd (mol %) | Ligand (mol %) | Solvent | Acid (mol %) | T[° C.] | CO p(bar) | Yield of isomeric diesters [%] |
|---|---|---|---|---|---|---|---|
| 1 | Pd(acac)$_2$(1) | Xantphos(1.5) | toluene | HCl (5) | 105 | 40 | 56 |
| 2 | Pd(acac)$_2$(1) | Xantphos(1.5) | toluene | HCl (5) | 105 | 40 | 25 |
| 3 | Pd(acac)$_2$(1) | Xantphos(1.5) | toluene | HCl (5) | 105 | 40 | 13 |
| 4 | Pd(acac)$_2$(1) | Xantphos(1.5) | toluene | HCl (5) | 105 | 40 | 30 |

Example 1.1

Table 1, Entry 1

A 4 ml glass vial is charged with [Pd(acac)$_2$] (3.77 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, crotyl alcohol (87 µl, 1 mmol), ethanol (175 µl, 3 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 1.2

Table 1, Entry 2

A 4 ml glass vial is charged with [Pd(acac)$_2$] (3.77 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, but-3-en-2-ol (87 µl, 1 mmol), ethanol (175 µl, 3 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 1.3

Table 1, Entry 3

A 4 ml glass vial is charged with [Pd(acac)$_2$] (3.77 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, 2-methylprop-2-en-1-ol (87 µl, 1 mmol), ethanol (175 µl, 3 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 1.4

Table 1, Entry 4

A 4 ml glass vial is charged with [Pd(acac)$_2$] (3.77 mg, 1 mol %), Xantphos (8.8 mg, 1.5 mol %), cinnamyl alcohol (134 mg, 1 mmol) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, 3-phenylprop-2-en-1-ol (87 µl, 1 mmol), methanol (123 µl, 3 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 2

Variation of the Alcohols (Table 2)

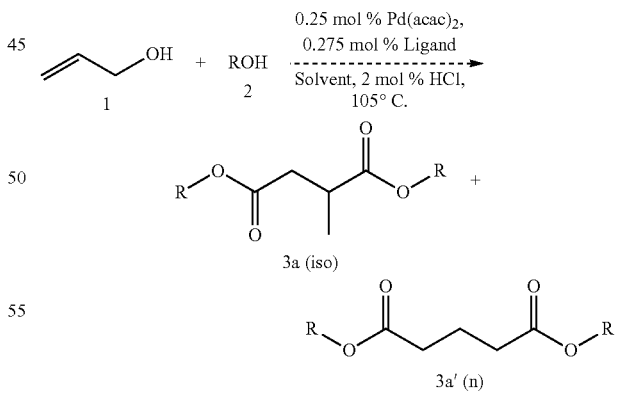

TABLE 2

| Entry | ROH | Yield (n:iso) |
|---|---|---|
| 1 | MeOH | 38 (58:42) |
| 2 | EtOH | 80 (58:42) |
| 3 | BuOH | 77 (55:45) |

TABLE 2-continued

| Entry | ROH | Yield (n:iso) |
|---|---|---|
| 4 | i-PrOH | 91 (60:40) |
| 5 | BnOH | 80 (62:38) |

Example 2.1

Table 2, Entry 1

A 4 ml glass vial is charged with [Pd(acac)z] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, methanol (123 µl, 3 mmol), allyl alcohol (68 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 2.2

Table 2. Entry 2

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, ethanol (175 µl, 3 mmol), allyl alcohol (68 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 2.3

Table 2, Entry 3

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 µl, 3 mmol), allyl alcohol (68 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 2.4

Table 2, Entry 4

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, isopropanol (230 µl, 3 mmol), allyl alcohol (68 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 2.5

Table 2, Entry 5

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, benzyl alcohol (310 µl, 3 mmol), allyl alcohol (68 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 3

Variation of the Palladium Precursor (Table 3)

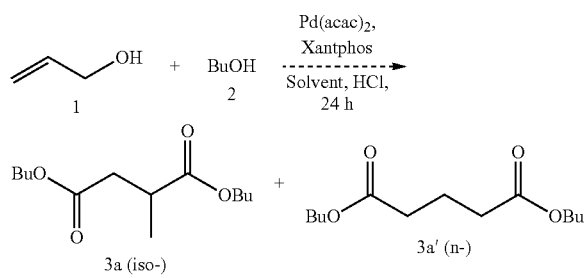

Example 3.1

Table 3, Entry 1

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 μl, 1 mmol), n-butanol (182 μl, 2 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 3.2

Table 3, Entry 2

A 4 ml glass vial is charged with [Pd(OAc)$_2$] (2.25 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 μl, 1 mmol), n-butanol (182 μl, 2 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 3.3

Table 3, Entry 3

A 4 ml glass vial is charged with [PdCl$_2$] (1.8 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 μl, 1 mmol), n-butanol (182 μl, 2 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released

TABLE 3

| Entry | [Pd](mol %) | L(mol %) | Solvent | Acid (mol %) | T[° C.] | p[bar] | Yield [%] (n:iso) |
|---|---|---|---|---|---|---|---|
| 1 | Pd(acac)$_2$(1) | Xantphos(1.5) | toluene | HCl (5) | 105 | 40 | 69 (54:46) |
| 2 | Pd(OAc)$_2$(1) | Xantphos(1.5) | toluene | HCl (5) | 105 | 40 | 64(53:47) |
| 3 | PdCl$_2$(1) | Xantphos(1.5) | toluene | HCl (5) | 105 | 40 | 61(53:47) |
| 4 | PdBr$_2$(1) | Xantphos(1.5) | toluene | HCl (5) | 105 | 40 | 42(63:37) |
| 5 | PdI$_2$(1) | Xantphos(1.5) | toluene | HCl (5) | 105 | 40 | 24(78:22) |
| 6 | Pd(COD)Cl$_2$(1) | Xantphos(1.5) | toluene | HCl (5) | 105 | 40 | 62(53:47) |
| 7 | Pd$_2$(dba)$_3$(0.5) | Xantphos(1.5) | toluene | HCl (5) | 105 | 40 | 70(57:43) |
| 8 | Pd(TFA)$_2$ | Xantphos(1.5) | toluene | HCl (5) | 105 | 40 | 72(56:44) |
| 9 | PdO(1) | Xantphos(1.5) | toluene | HCl (5) | 105 | 40 | 64(54:46) |
| 10 | Pd(NO$_3$)$_2$·2H$_2$O | Xantphos(1.5) | toluene | HCl (5) | 105 | 40 | 46(54:46) |
| 11 | (NH$_4$)$_2$PdCl$_6$ | Xantphos(1.5) | toluene | HCl (5) | 105 | 40 | 49(52:48) | gradually. The autoclave is purged three times with nitrogen. Subsequently, isooctane (100 µl) is added as internal standard. The yield and selectivity are determined by means of GC analysis.

Example 3.4

Table 3, Entry 4

A 4 ml glass vial is charged with [PdBr$_2$] (2.7 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 3.5

Table 3, Entry 5

A 4 ml glass vial is charged with [PdI$_2$] (3.6 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 3.6

Table 3, Entry 6

A 4 ml glass vial is charged with [Pd(COD)Cl$_2$] (2.9 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO. CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 3.7

Table 3, Entry 7

A 4 ml glass vial is charged with [Pd$_2$(dba)$_3$] (4.6 mg, 0.5 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 3.8

Table 3, Entry 8

A 4 ml glass vial is charged with [Pd(TFA)$_2$] (3.4 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 3.9

Table 3, Entry 9

A 4 ml glass vial is charged with PdO (1.21 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 3.10

Table 3, Entry 10

A 4 ml glass vial is charged with $Pd(NO_3)_2 \cdot 2H_2O$ (2.7 mg, 1 mol %). Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 3.11

Table 3, Entry 11

A 4 ml glass vial is charged with $(NH_4)_2PdCl_6$ (3.5 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO. CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 4

Variation of the Solvents (Table 4)

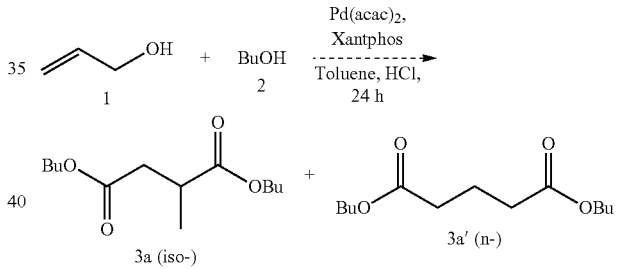

TABLE 4

| Entry | Pd (mol %) | Ligand (mol %) | Solvent | Acid (mol %) | T(° C.) | p(bar) | Yield of 3a + 3a' (n-/iso-) |
|---|---|---|---|---|---|---|---|
| 1 | Pd(acac)$_2$(1) | Xantphos(1.5) | toluene | HCl (5) | 105 | 40 | 70 (58:42) |
| 2 | Pd(acac)$_2$(1) | Xantphos(1.5) | dioxane | HCl (5) | 105 | 40 | 54 (56:44) |
| 3 | Pd(acac)$_2$(1) | Xantphos(1.5) | acetone | HCl (5) | 105 | 40 | 58(63:37) |
| 4 | Pd(acac)$_2$(1) | Xantphos(1.5) | butanol | HCl (5) | 105 | 40 | 8 (76:24) |
| 5 | Pd(acac)$_2$(1) | Xantphos(1.5) | THF | HCl (5) | 105 | 40 | 41 (60:40) |
| 6 | Pd(acac)$_2$(1) | Xantphos(1.5) | MeCN | HCl (5) | 105 | 40 | 55 (72:28) |
| 7 | Pd(acac)$_2$(1) | Xantphos(1.5) | anisole | HCl (5) | 105 | 40 | 58 (56:44) |

Example 4.1

Table 4, Entry 1

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, toluene (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 4.2

Table 4, Entry 2

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, dioxane (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 4.3

Table 4, Entry 3

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, acetone (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 4.4

Table 4, Entry 4

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, n-butanol (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 4.5

Table 4, Entry 5

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, THF (2 ml), allyl alcohol (68 µl, 1 mmol), n-butanol (182 µl, 2 mmol) and 1 M hydrochloric acid solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 4.6

Table 4, Entry 6

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, acetonitrile (2 ml), allyl alcohol (68 µl, 1 mmol), n-butanol (182 μl, 2 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

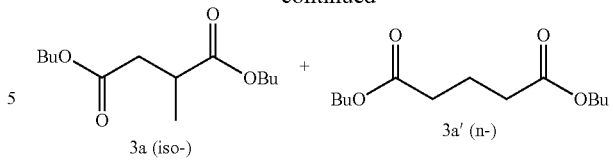

TABLE 5

| Entry | Pd (mol %) | Ligand (mol %) | Solvent | Acid (mol %) | T[° C.] | CO p(bar) | Yield (n-/iso-) |
|---|---|---|---|---|---|---|---|
| 1 | Pd(acac)$_2$(1) | Xantphos(1.5) | toluene | HCl (5) | 89 | 40 | 70 (58:42) |
| 2 | Pd(acac)$_2$(1) | Xantphos(1.5) | toluene | HCl (5) | 80 | 40 | 54 (56:44) |
| 3 | Pd(acac)$_2$(0.1) | Xantphos(0.15) | toluene | HCl (2) | 140 | 40 | 67(53) |
| 4 | Pd(acac)$_2$(0.25) | Xantphos(0.275) | toluene | HCl (2) | 105 | 10 | 15(62) |
| 5 | Pd(acac)$_2$(0.25) | Xantphos(0.275) | toluene | HCl (2) | 105 | 20 | 59(60) |
| 6 | Pd(acac)$_2$(0.25) | Xantphos(0.275) | toluene | HCl (2) | 105 | 40 | 73(58) |
| 7 | Pd(acac)$_2$(0.25) | Xantphos(0.275) | toluene | HCl (2) | 105 | 60 | 66(59) |
| 8 | Pd(acac)$_2$(0.25) | Xantphos(0.275) | toluene | HCl (2) | 120 | 40 | 74(56) |
| 9 | Pd(acac)$_2$(0.25) | Xantphos(0.275) | toluene | HCl (2) | 140 | 40 | 70(55) |

Example 4.7

Table 4, Entry 7

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, anisole (2 ml), allyl alcohol (68 μl, 1 mmol), n-butanol (182 μl, 2 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5

Variation of Pressure and Temperature, Amount of Acid, Ligand Ratio (Table 5):

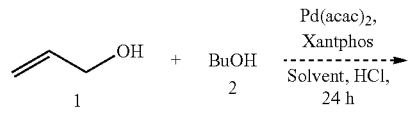

Example 5.1

Table 5, Entry 1

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO. CO is injected to 40 bar at room temperature. The reaction is conducted while stirring with a magnetic stirrer at 89° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.2

Table 5, Entry 2

A 4 ml glass vial is charged with [Pd(acac)$_2$] (3.04 mg, 1 mol %), Xantphos (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 80° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.3

Table 5, Entry 3

A 4 ml glass vial is charged with [Pd(acac)$_2$] (0.30 mg, 0.1 mol %), Xantphos (0.89 mg, 0.15 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 140° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.4

Table 5, Entry 4

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 10 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.5

Table 5, Entry 5

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 20 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.6

Table 5, Entry 6

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.7

Table 5, Entry 7

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 60 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.8

Table 5, Entry 8

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 120° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 5.9

Table 5, Entry 9

A 4 ml glass vial is charged with [Pd(acac)$_2$] (0.77 mg, 0.25 mol %), Xantphos (1.62 mg, 0.275 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (273 μl, 3 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO. CO is injected to 40 bar at room temperature. The reaction is conducted while stirring with a magnetic stirrer at 140° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 6

Variation of the Acid (Table 6)

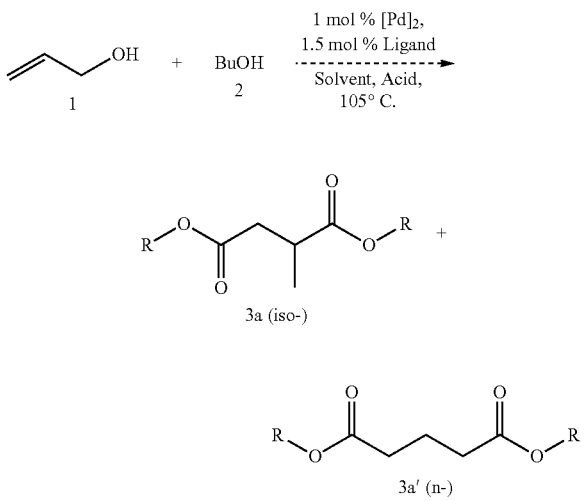

TABLE 6

| Entry | Pd (mol %) | Ligand (mol %) | Solvent | Acid (mol %) | T(° C.) | p(bar) | Yield (n-/iso-) |
|---|---|---|---|---|---|---|---|
| 1 | Pd(acac)$_2$(1) | Xantphos(1.5) | toluene | HCl (5) | 105 | 40 | 77 (54:46) |
| 2 | Pd(acac)$_2$(1) | Xantphos(1.5) | toluene | TsOH H$_2$O (5) | 105 | 40 | 0 |
| 3 | Pd(acac)$_2$(1) | Xantphos(1.5) | toluene | TFA (5) | 105 | 40 | 0 |
| 4 | Pd(acac)$_2$(1) | Xantphos(1.5) | toluene | MSA (5) | 105 | 40 | 0 |
| 5 | Pd(acac)$_2$(1) | Xantphos(1.5) | toluene | KCl (5) | 105 | 40 | 0 |
| 6 | Pd(acac)$_2$(1) | Xantphos(1.5) | toluene | LiCl (5) | 105 | 40 | 0 |
| 7 | Pd(acac)$_2$(1) | Xantphos(1.5) | THF | HBr(5) aqueous solution | 105 | 40 | 10(73:27) |
| 8 | Pd(acac)$_2$(1) | Xantphos(1.5) | THF | HCl (5) aqueous solution | 105 | 40 | 15(62:38) |
| 9 | Pd(acac)$_2$(1) | Xantphos(1.5) | toluene | HCl (5) ether solution + LiBr(5) | 105 | 40 | 32(67:33) |
| 10 | Pd(acac)$_2$(1) | Xantphos(1.5) | toluene | HCl (5) ether solution + LiBr(10) | 105 | 40 | 25(65:33) |
| 11 | Pd(acac)$_2$(1) | Xantphos(1.5) | toluene | HCl (5) ether solution + LiI(5) | 105 | 40 | 10(84:16) |
| 12 | Pd(acac)$_2$(1) | Xantphos(1.5) | toluene | HCl(5) Etherlösung + LiI(10) | 105 | 40 | 10(82:18) |

Example 6.1

Table 6, Entry 1

A 4 ml glass vial is charged with [Pd(acac)$_2$] (3.04 mg, 1 mol %). L1 (Xantphos) (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl alcohol (68 μl, 1 mmol) and 1 M hydrochloric acid solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 6.2

Table 6, Entry 2

A 4 ml glass vial is charged with [Pd(acac)$_2$] (3.07 mg, 1 mol %), L1 (Xantphos) (8.8 mg, 1.5 mol %), TsOH.H$_2$O (9.5 mg, 5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl alcohol (68 μl, 1 mmol) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 6.3

Table 6, Entry 3

A 4 ml glass vial is charged with [Pd(acac)$_2$] (3.07 mg, 1 mol %), L1 (Xantphos) (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl alcohol (68 μl, 1 mmol) and trifluoroacetic acid (TFA) (3.8 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 6.4

Table 6, Entry 4

A 4 ml glass vial is charged with [Pd(acac)$_2$] (3.07 mg, 1 mol %), L1 (Xantphos) (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl alcohol (68 μl, 1 mmol) and methanesulphonic acid (MSA) (3.2 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 6.5

Table 6, Entry 5

A 4 ml glass vial is charged with [Pd(acac)$_2$] (3.07 mg, 1 mol %), L1 (Xantphos) (8.8 mg, 1.5 mol %), potassium chloride (3.7 mg, 5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl alcohol (68 μl, 1 mmol) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 6.6

Table 6, Entry 6

A 4 ml glass vial is charged with [Pd(acac)$_2$] (3.07 mg, 1 mol %), L1 (Xantphos) (8.8 mg, 1.5 mol %), lithium chloride (2.1 mg, 5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 6.7

Table 6, Entry 7

A 4 ml glass vial is charged with [Pd(acac)$_2$] (3.07 mg, 1 mol %), L1 (Xantphos) (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of THF, n-butanol (182 µl, 2 mmol), allyl alcohol (68 µl, 1 mmol) and 1 M aqueous HBr solution (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 6.8

Table 6, Entry 8

A 4 ml glass vial is charged with [Pd(acac)$_2$] (3.07 mg, 1 mol %), L1 (Xantphos) (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of THF, n-butanol (182 µl, 2 mmol), allyl alcohol (68 µl, 1 mmol) and 1 M aqueous HCl solution (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 6.9

Table 6, Entry 9

A 4 ml glass vial is charged with [Pd(acac)$_2$] (3.07 mg, 1 mol %), L1 (Xantphos) (8.8 mg, 1.5 mol %), LiBr (4.5 mg, 5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 6.10

Table 6, Entry 10

A 4 ml glass vial is charged with [Pd(acac)$_2$] (3.07 mg, 1 mol %), L1 (Xantphos) (8.8 mg, 1.5 mol %), LiBr (9 mg, 10 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere.

After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 6.11

Table 6, Entry 11

A 4 ml glass vial is charged with [Pd(acac)$_2$] (3.07 mg, 1 mol %), L1 (Xantphos) (8.8 mg, 1.5 mol %), LiI (6.6 mg, 5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon.

Through this cannula, 2 ml of toluene, n-butanol (182 μl, 2 mmol), allyl alcohol (68 μl, 1 mmol) and 1 M HCl solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 6.12

Table 6, Entry 12

A 4 ml glass vial is charged with [Pd(acac)$_2$] (3.07 mg, 1 mol %), L1 (Xantphos) (8.8 mg, 1.5 mol %), LiI (13.3 mg, 10 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl alcohol (68 μl, 1 mmol) and 1 M HCl solution in diethyl ether (50 μl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 μl) is added as internal standard. The yield and selectivity are determined by means of GC analysis.

Example 7

Variation of Ligand (Table 7):

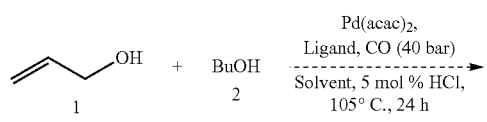

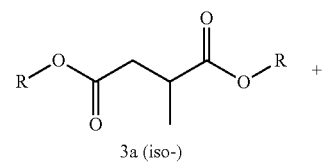
3a (iso-)

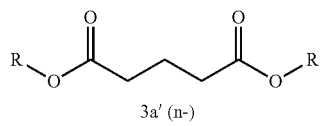
3a' (n-)

TABLE 7

| Entry | Ligand | Yield % (n:iso) |
|---|---|---|
| 1 | L1 | 71% (n:iso = 54:49) |
| 2 | L2 | 28% n:iso = 34:66 |
| 3 | L3 | 41% n:iso = 49:51 |
| 4 | L4 | 28% n:iso = 27:73 |
| 5 | L5 | 56% n:iso = 47:53 |
| 6 | L6 | 24% n:iso = 34:66 |

TABLE 7-continued

| Entry | Ligand | Yield % (n:iso) |
|---|---|---|
| 7 | L7 | 13% n:iso = 25:75 |
| 8 | L8 | R = 2-Me—Ph 29% n:iso = 15:85 |
| 9 | L9 | 53% n:iso = 85:15 |
| 10 | L10 | 15% n:iso = 64:36 |
| 11 | BuPAd₂ L11 | 31% n:iso = 25:75 |
| 12 | L12 | 15% n:iso = 21:79 |

Example 7.1

Table 7, Entry 1

A 4 ml glass vial is charged with [Pd(acac)$_2$] (3.07 mg, 1 mol %), L1 (Xantphos) (8.8 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.2

Table 7, Entry 2

A 4 ml glass vial is charged with [Pd(acac)$_2$] (3.07 mg, 1 mol %), L2 (10,10'-(oxybis(2,1-phenylene))bis(10H-phenoxaphosphinine)) (8.5 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.3

Table 7, Entry 3

A 4 ml glass vial is charged with [Pd(acac)$_2$] (3.07 mg, 1 mol %), L3 (2,2'-((9,9-dimethyl-9H-xanthene-4,5-diyl)bis(tert-butylphosphinediyl))dipyridine) (8.1 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.4

Table 7, Entry 4

A 4 ml glass vial is charged with [Pd(acac)$_2$] (3.07 mg, 1 mol %). L4 ((oxybis(2,1-phenylene))bis(tert-butyl(phenyl) phosphine)) (7.5 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.5

Table 7, Entry 5

A 4 ml glass vial is charged with [Pd(acac)$_2$] (3.07 mg, 1 mol %), L5 (4,6-bis(diphenylphosphinyl)-10H-phenoxazine) (8.3 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.6

Table 7, Entry 6

A 4 ml glass vial is charged with [Pd(acac)$_2$] (3.07 mg, 1 mol %), L6 (1,3-bis((diphenylphosphinyl)methyl)benzene) (7.1 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.7

Table 7, Entry 7

A 4 ml glass vial is charged with [Pd(acac)$_2$] (3.07 mg, 1 mol %), L7 ((oxybis(2,1-phenylene))bis(di-tert-butylphosphine)) (6.9 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.8

Table 7, Entry 8

A 4 ml glass vial is charged with [Pd(acac)$_2$] (3.07 mg, 1 mol %), L8 ((oxybis(2,1-phenylene))bis(di-o-tolylphosphine) (8.9 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.9

Table 7, Entry 9

A 4 ml glass vial is charged with [Pd(acac)$_2$] (3.07 mg, 1 mol %), L9 (bis(2-(diphenylphosphinyl)-5-methylphenyl)methane) (8.5 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.10

Table 7, Entry 10

A 4 ml glass vial is charged with [Pd(acac)$_2$] (3.07 mg, 1 mol %), L10 (1,2-bis((di-tert-butylphosphinyl)methyl)benzene) (5.91 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.11

Table 7, Entry 11

A 4 ml glass vial is charged with [Pd(acac)$_2$] (3.07 mg, 1 mol %), L11 (di-1-adamantylbutylphosphine) (11 mg, 3 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

Example 7.12

Table 7, Entry 12

A 4 ml glass vial is charged with [Pd(acac)$_2$] (3.07 mg, 1 mol %), L12 (1-(2-(diphenylphosphinyl)benzyl)-1H-pyrrole) (10.2 mg, 3 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl alcohol (68 µl, 1 mmol) and 1 M HCl solution in diethyl ether (50 µl, 5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 105° C. for 24 hours. After the end of the reaction, the autoclave is cooled down and the pressure is released gradually. The autoclave is purged three times with nitrogen. Subsequently, isooctane (100 µl) is added as internal standard. The yield and selectivity are determined by means of GC analysis.

The invention claimed is:

1. Process for doubly carbonylating allyl alcohols to diesters, comprising: reacting, in a single step, a linear or branched allyl alcohol with a linear or branched alkanol with supply of CO and in the presence of a catalytic system composed of a palladium complex and at least one organic phosphorus ligand and in the presence of a hydrogen halide selected from HCl, HBr and HI, wherein both the allyl portion and the alcohol portion of the allyl alcohol are reacted with the CO.

2. Process according to claim 1, characterized in that the allyl alcohols are compounds of the general formula (1):

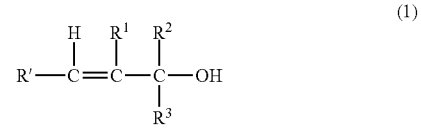

(1)

where $R^1$, $R^2$ and $R^3$ are independently hydrogen or a $C_1$ to $C_{10}$ alkyl radical and R' is hydrogen, or a saturated branched or unbranched, aliphatic, cycloaliphatic or cycloaliphatic-aliphatic hydrocarbyl radical having up to 12 carbon atoms, in which C—C bonds may be interrupted by oxygen or the —O—CO— group, or a phenyl radical, where the phenyl radical may be substituted as follows: $C_1$- to $C_{10}$-alkyl- or $C_1$- to $C_{10}$-alkoxy groups.

3. Process according to claim 1,
characterized in that the alkanols are compounds of the general formula ROH where R is a $C_1$- to $C_{20}$-alkyl, a $C_1$ to $C_{20}$-cycloalkyl or a $C_7$- to $C_{11}$-aralkyl group.

4. Process according to claim 1,
characterized in that the reaction is conducted in the liquid phase at a temperature of 70 to 250° C.

5. Process according to claim 1,
characterized in that reaction is conducted under a pressure of 2 to 100 bar.

6. Process according to claim 1,
characterized in that the palladium complex is formed in situ proceeding from a pre-complex, using, as palladium source, palladium-containing salts and complexes as precursor.

7. Process according to claim 6,
characterized in that the palladium complex is selected from the group comprising Pd acetate, Pd acetylacetonate, Pd halides, Pd-halogen-1,5-cyclooctadienes, Pd nitrates, Pd oxide and diammonium hexachloropalladate.

8. Process according to claim 1,
characterized in that the phosphine ligands have a mono- or bidentate structure, preferably selected from the group comprising L1—(9,9-dimethyl-9H-xanthene-4,5-diyl)bis(diphenylphosphine),
L2—10,10'-(oxybis(2,1-phenylene))bis(10H-phenoxaphosphinine),
L3—2,2'-((9,9-dimethyl-9H-xanthene-4,5-diyl)bis(tert-butylphosphinediyl))dipyridine,
L4—(oxybis(2,1-phenylene))bis(tert-butyl(phenyl)phosphine),
L5—4,6-bis(diphenylphosphinyl)-10H-phenoxazine,
L6—1,3-bis((diphenylphosphinyl)methyl)benzene,
L7—(oxybis(2,1-phenylene))bis(di-tert-butylphosphine),
L8—(oxybis(2,1-phenylene))bis(di-o-tolylphosphine),
L9—bis(2-(diphenylphosphinyl)-5-methylphenyl)methane,
L10—1,2-bis((di-tert-butylphosphinyl)methyl)benzene,
L11—di(1-adamantyl)-n-butylphosphine,
L12—1-(2-(diphenylphosphinyl)benzyl)-1H-pyrrole.

9. Process according to claim 1,
characterized in that the hydrogen halide used is hydrogen chloride.

10. Process according to claim 1,
characterized in that the ratio of palladium to hydrogen halide is in the range from 1:3 to 1:30.

11. Process according to claim 1,
characterized in that a metal halide is added to the reaction, where the ratio of halide to hydrogen halide is in the range from 1:1 to 5:1.

\* \* \* \* \*